United States Patent
Reil et al.

(10) Patent No.: US 10,548,376 B2
(45) Date of Patent: Feb. 4, 2020

(54) DISPOSABLE HAND OPERATED CARTRIDGE BODY PIERCING INSTRUMENT

(71) Applicant: Goran Reil, Gardena, CA (US)

(72) Inventors: Vladimir Reil, Rancho Palos Verdes, CA (US); Goran Reil, Las Vegas, NV (US)

(*) Notice: Subject to any disclaimer, the term of this patent is extended or adjusted under 35 U.S.C. 154(b) by 315 days.

(21) Appl. No.: 15/276,609

(22) Filed: Sep. 26, 2016

(65) Prior Publication Data

US 2018/0055160 A1    Mar. 1, 2018

Related U.S. Application Data

(60) Provisional application No. 62/378,638, filed on Aug. 23, 2016.

(51) Int. Cl.
*A61B 17/34* (2006.01)
*A44C 7/00* (2006.01)

(52) U.S. Cl.
CPC ............. *A44C 7/001* (2013.01); *A61B 17/34* (2013.01)

(58) Field of Classification Search
CPC ........... A44C 7/00; A44C 7/001; A44C 7/003; A61B 17/00; A61B 17/34; A61B 2017/0023
See application file for complete search history.

(56) References Cited

U.S. PATENT DOCUMENTS

| | | |
|---|---|---|
| 4,030,507 A | 6/1977 | Mann |
| 4,146,032 A | 3/1979 | Rubenstein et al. |
| 4,474,572 A | 10/1984 | McNaughton et al. |
| 4,527,563 A | 7/1985 | Reil |
| 5,004,471 A | 4/1991 | Mann |
| 5,263,960 A | 11/1993 | Mann |
| 5,389,105 A | 2/1995 | Mann |

(Continued)

FOREIGN PATENT DOCUMENTS

| | | |
|---|---|---|
| EP | 1297760 A2 | 4/2003 |
| JP | S60158413 U | 10/1985 |
| JP | 2008237267 | 10/2008 |

OTHER PUBLICATIONS

PCT International Search Report and Written Opinion of International Application No. PCT/US2017/047942, dated Aug. 11, 2017.

*Primary Examiner* — Vi X Nguyen
(74) *Attorney, Agent, or Firm* — Canady & Lortz LLP; Bradley K. Lortz

(57) ABSTRACT

Apparatuses and systems for ornamental piercing of body parts are disclosed comprising a main housing having a thumb grip section along a rear surface, a post holder including separate portions held together slidably engaged within a post holder track within the main housing such that the separate portions support a post while held together within the post holder track and fall away to release the post after exiting the post holder track, and a jaw slidably engaged with the main housing with a jaw track. The jaw track is parallel to the post holder track and the jaw supports a backing platform for piercing with the post as the jaw and main housing are moved together along the jaw track. The jaw includes a finger grip section disposed below and opposite the backing platform and opposite the thumb grip section of the main housing.

12 Claims, 10 Drawing Sheets

(56) References Cited

U.S. PATENT DOCUMENTS

| | | |
|---|---|---|
| 5,395,381 A | 3/1995 | Green et al. |
| D366,316 S | 1/1996 | Reil |
| 5,496,343 A | 3/1996 | Reil |
| 5,499,993 A | 3/1996 | Blomdahl et al. |
| D384,302 S | 9/1997 | Reil |
| 5,709,700 A | 1/1998 | Hirota |
| D392,042 S | 3/1998 | Reil |
| 5,792,170 A | 8/1998 | Reil |
| 5,868,774 A | 2/1999 | Reil |
| 5,913,869 A | 6/1999 | Reil |
| 6,036,712 A | 3/2000 | Blomdahl |
| 6,048,355 A | 4/2000 | Mann et al. |
| 6,074,406 A | 6/2000 | Mann |
| 6,099,545 A | 8/2000 | Mann et al. |
| 6,599,306 B1 * | 7/2003 | Reil ........................ A44C 7/001 606/188 |
| 7,955,349 B2 | 6/2011 | Reil |

* cited by examiner

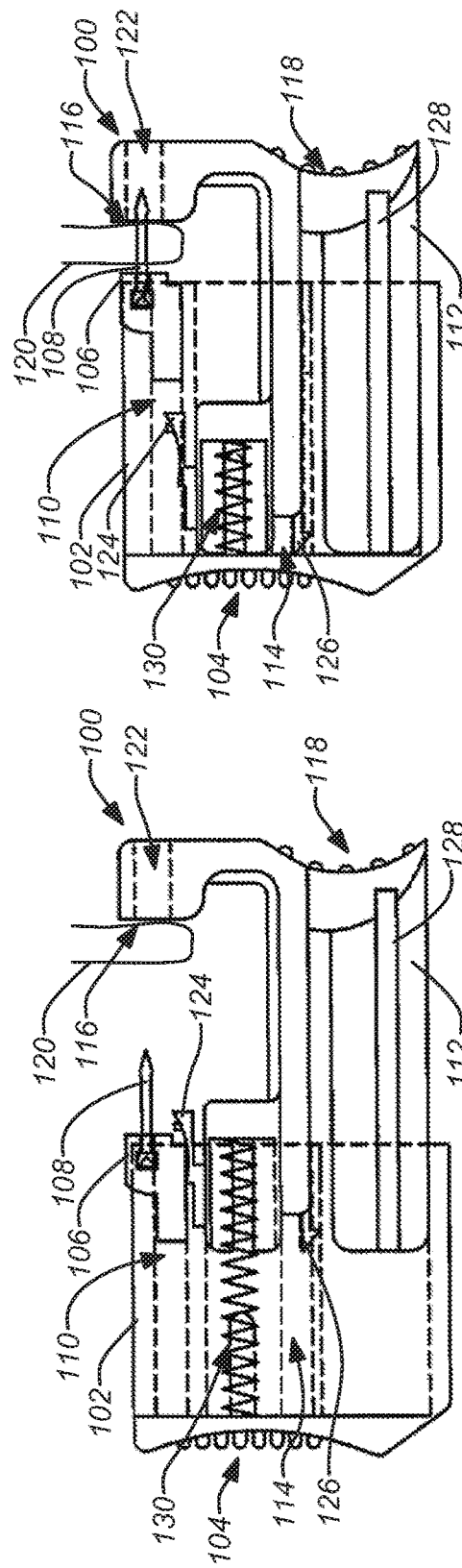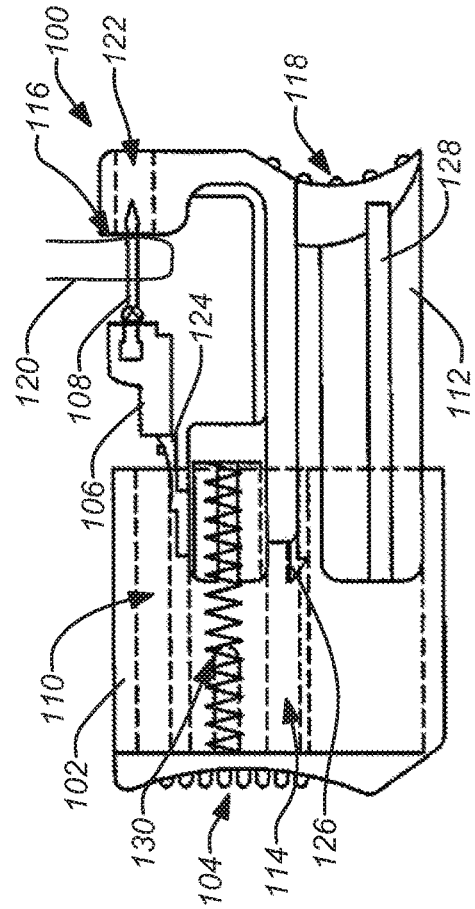
FIG. 1G
FIG. 1H
FIG. 1I

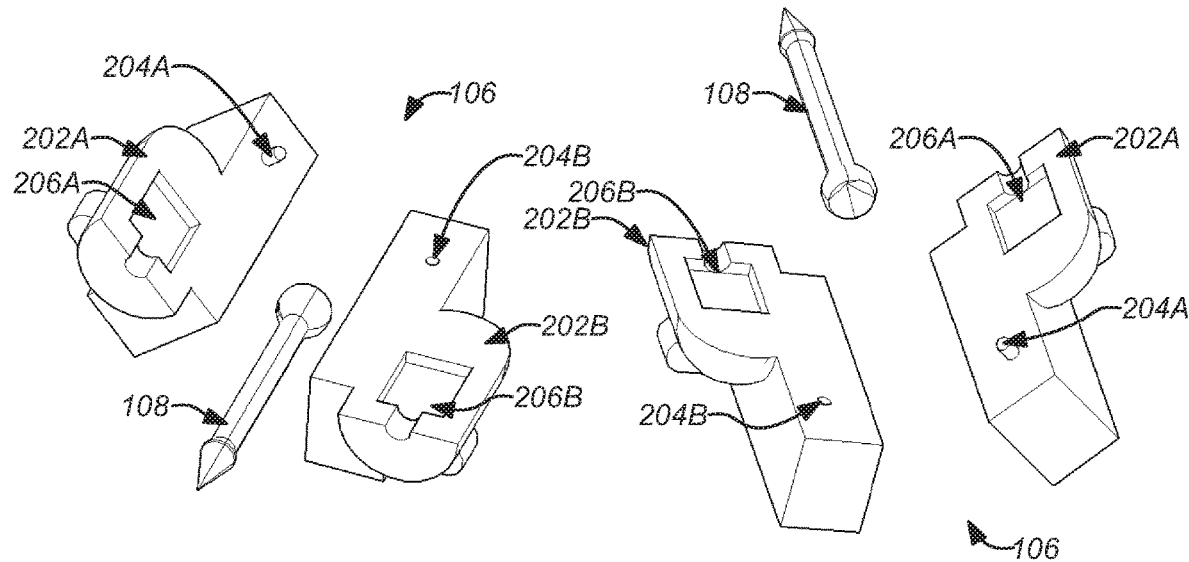
FIG. 2A
FIG. 2B
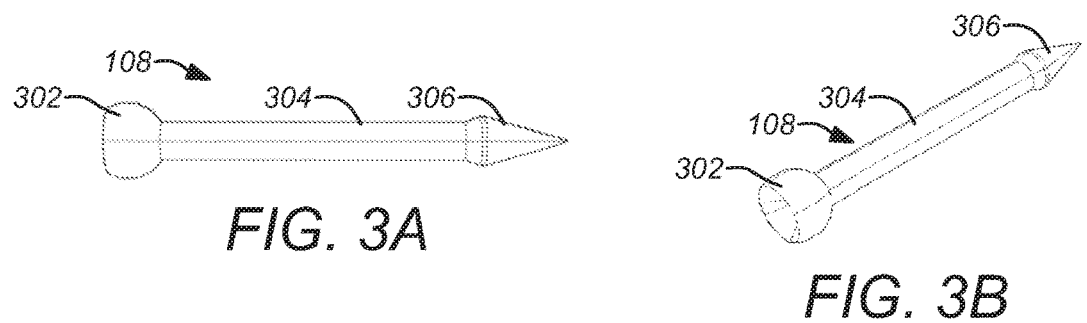
FIG. 3A
FIG. 3B
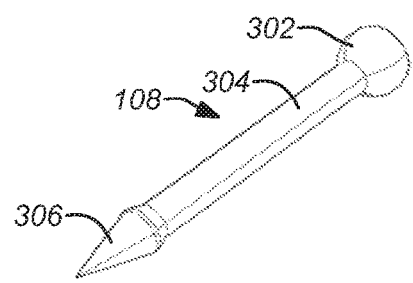
FIG. 3C

DISPOSABLE HAND OPERATED CARTRIDGE BODY PIERCING INSTRUMENT

CROSS-REFERENCE TO RELATED APPLICATIONS

This application claims the benefit under 35 U.S.C. § 119(e) of the following U.S. provisional patent application, which is incorporated by reference herein;

U.S. Provisional Patent Application No. 62/378,638, filed Aug. 23, 2016, and entitled "DISPOSABLE HAND OPERATED CARTRIDGE BODY PIERCING INSTRUMENT," by Reil et al.

BACKGROUND OF THE INVENTION

1. Field of the Invention

The present invention relates to apparatuses and methods, for ornamental piercing of body parts. Particularly, the present invention relates to apparatuses and methods for a disposable hand-operated cartridge body piercing instrument.

2. Description of the Related Art

In recent years, body piercing has become an increasingly common practice in the U.S. and throughout the world. Although the piercing of body parts is ancient, the practice is rapidly becoming a routine procedure, often performed by laypersons without medical experience or training. It is also important to understand that mainstream body piercing has evolved to include piercing of body parts other than just the ear. For example, piercing of flesh near the naval or belly button, eyebrow, lip, etc., are presently much more common than previously. Presently, a number of manually operated devices are available that allow for the safe, hygienic, user-friendly piercing of body parts. Examples of such systems are disclosed in U.S. Pat. No. 5,496,343 by Reil, issued Mar. 5, 1996, U.S. Pat. No. 5,792,170 by Reil, issued Aug. 11, 1998, U.S. Pat. No. 5,868,774 by Reil, issued Feb. 9, 1999, U.S. Pat. No. 6,599,306 by Reil, issued Jul. 29, 2003, and U.S. Pat. No. 6,796,990 by Reil, issued Sep. 28, 2004, all of which are incorporated by reference herein.

In addition to piercing entirely by hand with a needle, there are a variety of body piercing systems available today. These various body piercing systems essentially comprise a stud (also called an earring or a piercing earring) which includes an affixed ornamental piece with a post (also called a stud, pin or a piercing pin) and a nut (sometimes called a clasp) that are mounted in a cartridge. During the piercing process, the body part (e.g., an ear lobe) is placed between the post and the nut and the cartridge is squeezed, either by hand or by operating it in a special body piercing system (or "gun," instrument or assembly), which causes the post to pierce the body part and engage the nut. One particular body piercing assembly employs separate carriers for both of the post and the nut which are separately engaged into different locations of the body piercing assembly before piercing.

For example, U.S. Pat. No. 4,527,563, issued Jul. 9, 1985, to Reil, discloses an ear stud emplacement system that embodies a guntype stud setting member wherein sterility in high hygiene conditions are maintained in the piercing of ears and the setting of studs or posts, thereinto in secure relationship with the back clasp or nut of the stud or post. The improved system utilizes a stud gun having the components that come in contact with the earlobe and the like, that are disposable. The system allows for emplacement of sterile components and the placement of stud and back in the ear under sterile conditions not requiring touching of, for example, the stud and clasp with human hands or the touching of the replaceable components of the stud gun with human hands thereby decreasing the risk involved, of one getting their ears pierced.

In addition, U.S. Pat. No. 4,921,494, issued May 1, 1990, to Reil, discloses a disposable stud carrier and one-piece earring carrier for holding a clasp for attachment to an earring stud and providing a guide to direct the forward movement of the stud into the clasp. The earring carrier is used in conjunction with a stud gun having a protuberance upon its end of which the earring carrier may be positioned upon and so held.

One difficulty associated with piercing systems employing separate carriers for the nut and post is that each carrier must be separately installed into the piercing system before use. The separate carriers may be small and difficult to handle. The post and the nut must each be securely held in their respective carriers in proper alignment for the piercing. In addition, each carrier must be securely engaged to the piercing system when installed. In the case of the post carrier, occasionally the post may become dislodged from the carrier and fall to the floor. On the other hand, the nut carrier may accidentally become disengaged from the piercing instrument. In any such event, any components that are dropped must be discarded because they are no long hygienic.

Like any product, it is also desirable to produce piercing instruments at reduced costs. Every additional manufacturing step adds additional cost to the end product. For example, current a conventional body piercing instrument that employs separate carriers for the nut and post has a metal flange that is welded to a cylindrical portion that is used to engage the nut carrier. Although a welded flange is cheaper than machining the entire part from larger stock, eliminating the need for a welded flange would present a cheaper alternative. However, such a solution would need to first meet the requirements of providing secure engagement and alignment of the nut carrier to the body piercing instrument.

Inevitably, there are differences among the different manufactured units of any product. Thus, it is desirable that the design of a product accommodates the full range of manufacturing tolerances between mating parts that will result across the produced units. Meeting this objective results in greater customer satisfaction and fewer returned defective components. Prior art post carriers for body piercing instruments which are designed to hold the ornament of a post through a press fit (or interference fit) between the largest outer dimension of the ornament and the inner diameter of a cylindrical wall may yield inconsistent holding force applied to the post. The resulting holding force from a such a press fit engagement can vary widely with only very small changes in the difference between the ornament size and the cylindrical recess diameter. While improving manufacturing tolerances between the parts may address the issue, this would also involve additional costs. (Molded plastic components are inexpensive but difficult to maintain to tight tolerances, for example. Machined parts would be more precise but much more costly.) Thus, ordinary manufacturing tolerances between the ornament and a molded plastic post carrier can easily yield either too flimsy or too rigid an engagement between the ornament and the post carrier. In the former case, the post might fall out of the carrier during handling before piercing and in the latter case, the post may be difficult to remove from the carrier after piercing resulting in discomfort to the recipient.

In view of the foregoing, there is a need for apparatuses and systems that provide for simple, accurate, repeatable and safe body piercing. There is a need for methods and apparatuses for piercing systems to allow efficient and hygienic loading of separate carriers for the nut and post. There is particularly a need for such methods and apparatuses that provide separate carriers for the nut and post that are more easily manipulated and that operate with a reduced likelihood that sterile components may be dropped during loading. Further, there is also a need for such methods and apparatuses to reduce manufacturing costs, e.g. by reducing the cost of disposable parts. There is a need for designs that yield consistent performance without requiring precision manufacturing tolerances. There is also a need for such methods and apparatuses to employ standard components which can be employed with different piercing techniques. As discussed hereafter, the present invention meets these and other needs.

SUMMARY OF THE INVENTION

Apparatuses and systems for ornamental piercing of body parts are disclosed comprising a main housing having a thumb grip section along a rear surface, a post holder including separate portions held together slidably engaged within a post holder track within the main housing such that the separate portions support a post while held together within the post holder track and fall away to release the post after exiting the post holder track, and a jaw slidably engaged with the main housing with a jaw track. The jaw track is parallel to the post holder track and the jaw supports a backing platform for piercing with the post as the jaw and main housing are moved together along the jaw track. The jaw includes a finger grip section disposed below and opposite the backing platform and opposite the thumb grip section of the main housing.

A typical embodiment of the invention comprises a body piercing instrument cartridge, including a main housing having a thumb grip section along a rear surface, a post holder supporting a post and slidably engaged with a post holder track within the main housing, and a jaw slidably engaged with the main housing with a jaw track. The jaw track is parallel to the post holder track, and the jaw supports a backing platform for piercing a body part with the post as the jaw and main housing are moved together along the jaw track. The jaw includes a finger, grip section disposed below and opposite the backing platform and opposite the thumb grip section of the main housing. The post can comprise a conical barb for clutchless piercing. the finger grip section and the thumb grip section can each comprise a series of bumps or ridges for improving grip.

In some embodiments, the jaw can include a stiffener disposed behind finger grip section. The stiffener can comprise a longitudinal stiffener extending from the finger grip section parallel to the jaw track into the main housing. The stiffener can also form an additional track between the main housing and the jaw. The stiffener stabilizes movement of the jaw and main body during piercing.

In further embodiment, the post holder can include separate portions held together to support the post while slidably engaged with the post holder track within the main housing such that the separate portions fall away to release the post after exiting the post holder track.

A spring can typically be disposed between the main housing and the jaw to oppose to moving the jaw and main housing together. The jaw can includes a catch for holding the jaw engaged in the jaw track of the main housing against the spring forcing the jaw and the main housing apart. In addition, the jaw can include a push catch for sliding past the post holder as the jaw and main housing are moved together during piercing to engage a back end of the post holder and push the post holder out of the post holder track as the spring forces the jaw and main housing apart after piercing.

In some embodiments, the backing platform can comprise a surface for supporting a user body part in an area around a back side of a piercing location and hole therethough aligned with the post. The hole therethough can be vertically elongated to accommodate some vertical movement by the post during piercing.

In further embodiments, the backing platform can house a clutch disposed in a vertical slot to engage the post during piercing and then slide out of the vertical slot.

In a similar manner, a typical method embodiment of the invention comprises a method of piercing a body part, including the steps of disposing a body part against a backing platform of a jaw, the jaw slidably engaged with a main housing with a jaw track and the body part between the jaw and a post supported in a post holder and slidably engaged with a post holder track within the main housing parallel to the jaw track, disposing one or more fingers of a user's hand across a finger grip section disposed below and opposite the backing platform of the jaw and having a stiffener behind the finger grip section aligned parallel with the jaw track, disposing a thumb of the user's hand across a thumb grip section along a rear surface of the main body, and applying pressure between the thumb and one or more fingers to move the jaw and the main body together along the jaw track such that a post pierces the body part against the backing platform of the jaw.

BRIEF DESCRIPTION OF THE DRAWINGS

Referring now to the drawings in which like reference numbers represent corresponding parts throughout:

FIG. 1G illustrates a cross section view of an exemplary hand operated body piercing cartridge embodiment of the invention prepared for use;

FIG. 1H illustrates a cross section view of an exemplary hand operated body piercing cartridge embodiment of the invention in use compressed to pierce a body part;

FIG. 1I illustrates a cross section view of an exemplary operated body piercing cartridge embodiment of the invention in use released to eject the post holder;

FIG. 2A illustrates a front isometric view of an exemplary post holder for use in a hand operated body piercing cartridge embodiment of the invention;

FIG. 2B illustrates a back isometric view of an exemplary post holder for use in a hand operated body piercing cartridge embodiment of the invention;

FIG. 3A illustrates a side view of an exemplary conical barb post for use with a band operated body piercing cartridge embodiment of the invention;

FIG. 3B illustrates a rear isometric view of an exemplary conical barb post for use with a hand operated body piercing cartridge embodiment of the invention;

FIG. 3C illustrates a front isometric view of an exemplary conical barb post for use with a hand operated body piercing cartridge embodiment of the invention;

DETAILED DESCRIPTION OF THE PREFERRED EMBODIMENT

Figure 1A:
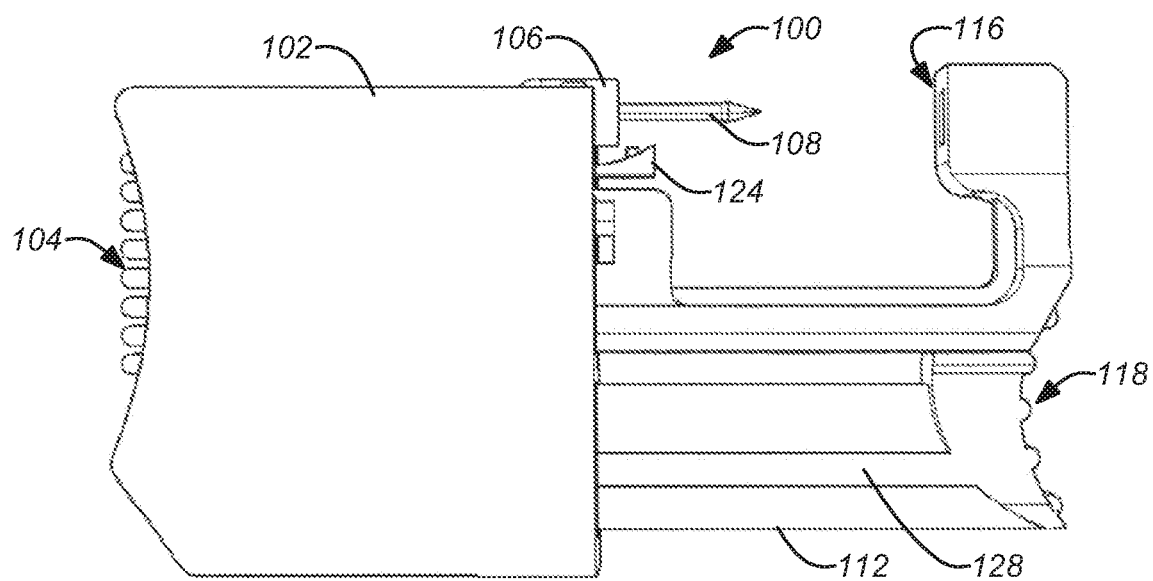
FIG. 1A illustrates a side view of an exemplary hand operated body piercing cartridge embodiment of the invention.
Figure 1B:
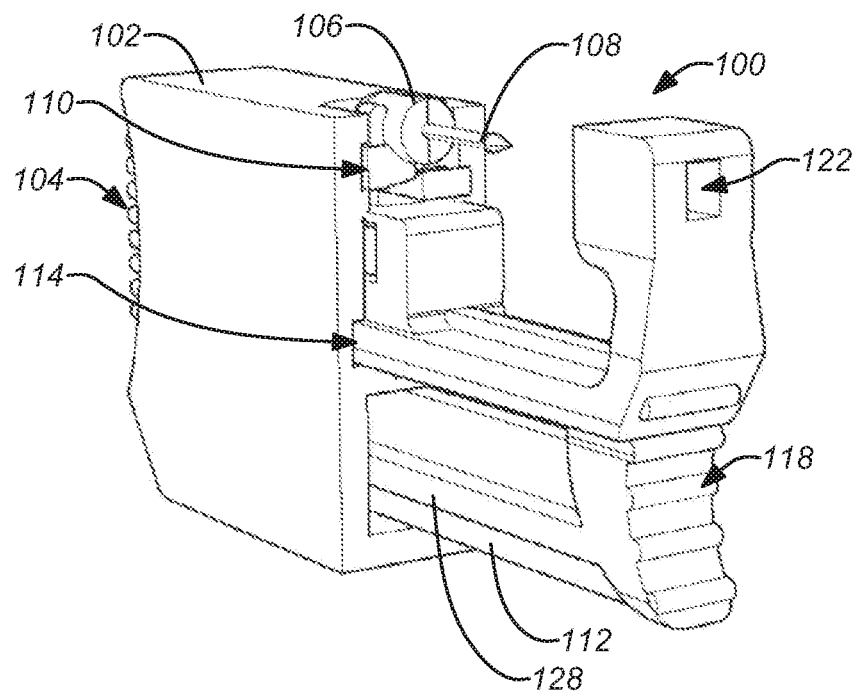
FIG. 1B illustrates another view of an exemplary hand operated body piercing cartridge embodiment of the invention.
Figure 1C:
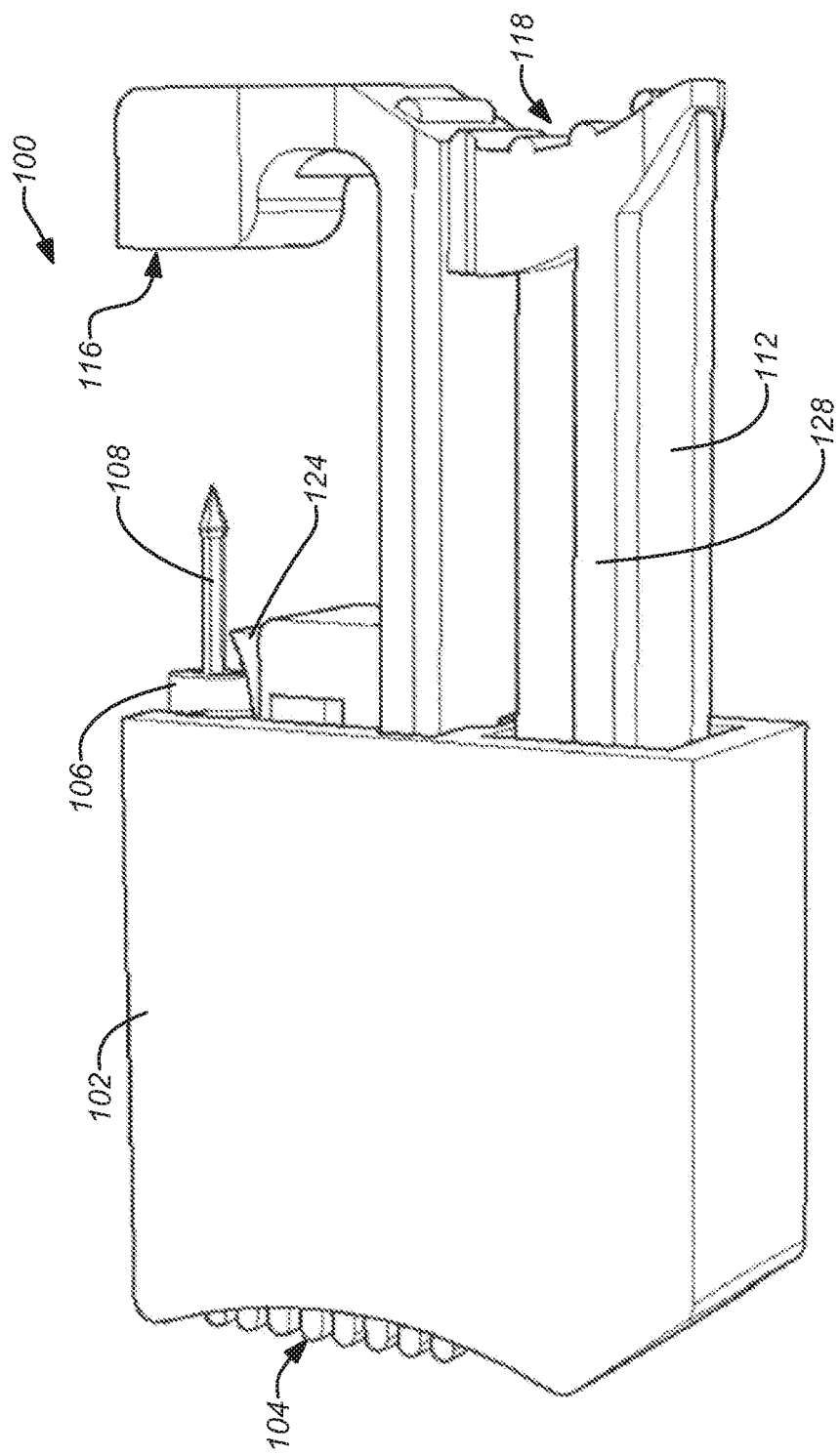
FIG. 1C illustrates a lower side view of an exemplary hand operated body piercing cartridge embodiment of the invention.
Figure 1D:
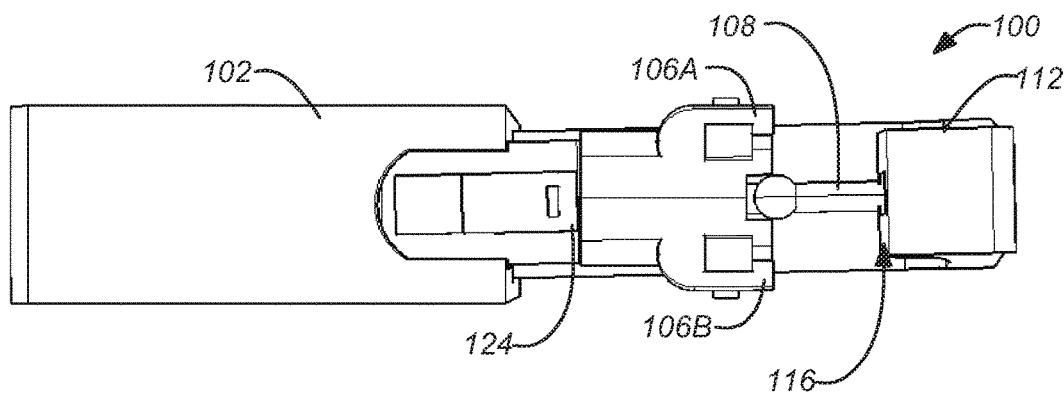
FIG. 1D illustrates a top view of an exemplary hand operated body piercing cartridge embodiment of the invention showing the post carrier open after piercing.
Figure 1E:
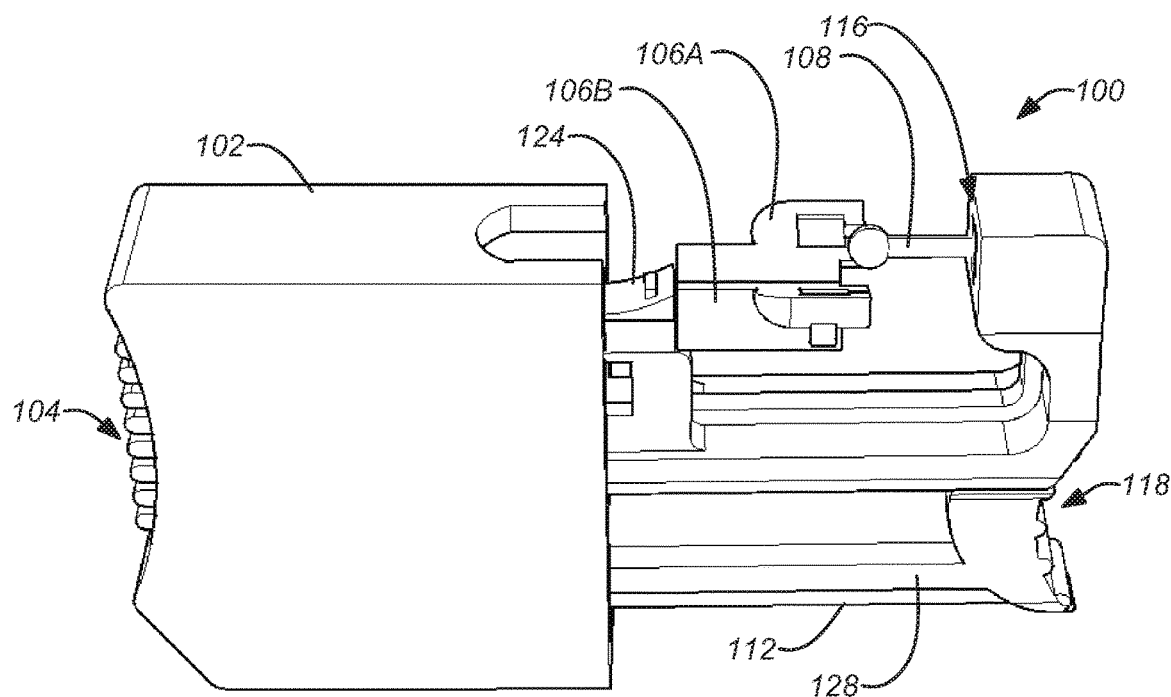
FIG. 1E illustrates an upper side view of an exemplary hand operated body piercing cartridge embodiment of the invention showing the post carrier open after piercing.
Figure 1F:
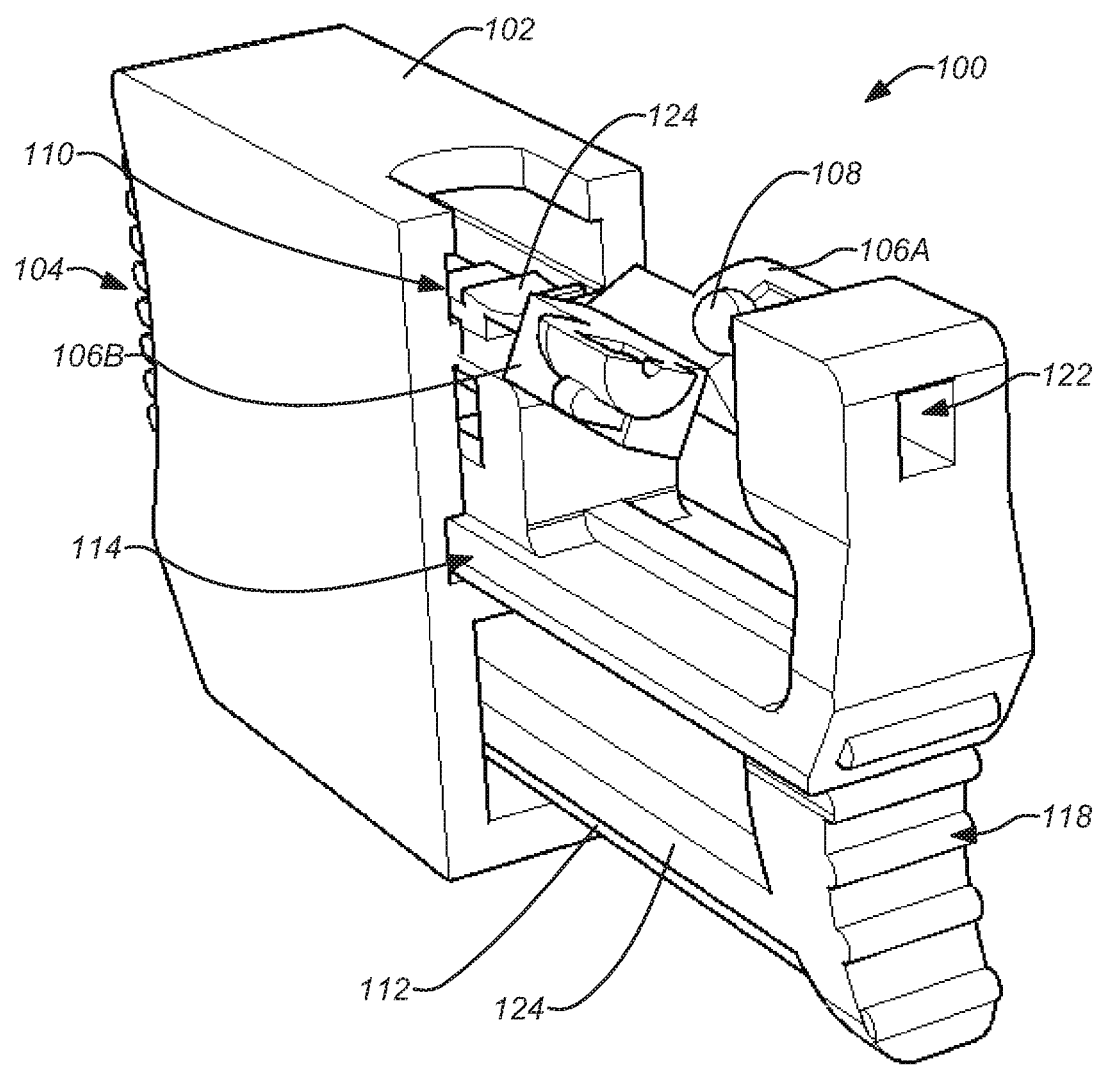
FIG. 1F illustrates an upper front view of an exemplary hand operated body piercing cartridge embodiment of the invention showing the post carrier open after piercing.

In the following description including the preferred embodiment, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

1.0 Disposable Hand Operated Cartridge Body Piercing Instrument

As mentioned above, various embodiments of the invention are designed to be used with and encompass a body piercing cartridge for ornamental piercing of body parts. Embodiments of the invention are particularly suited for piercing of the nose, although they can be employed in piercing almost any body part as will be understood by those skilled in the art. Embodiments of the invention provide a compact and disposable device that is hand operated. Typically, the device comes in a sealed sterilized package. The cartridge is pre-loaded with the post (which includes a stud ornament) so that it can be readily operated to create a body part piercing and then discarded.

FIGS. 1A to 1F illustrate various views of an exemplary hand operated body piercing cartridge embodiment of the invention. The body piercing instrument cartridge 100 includes a main housing 102 having a thumb grip section 104 along a rear surface. A post holder 106, which supports a post 108, is slidably engaged with a post holder track 110 within the main housing 102. A jaw 112 is slidably engaged with the main housing 102 with a jaw track, the jaw track 114 parallel to the post holder track 110. The jaw 112 supports a backing platform 116 for piercing a body part with the post 108 as the jaw 112 and main housing 102 are moved together along the jaw track 114. The jaw 112 also includes a finger grip section 118 disposed below and opposite the backing platform 116 and opposite the thumb grip section 104 of the main housing 102.

Typically, embodiments of the invention can be produced from injection molded plastic materials that can be sterilized although any other suitable material is also possible. Any of the separate moldings for the main housing 102, jaw 112, and post holder 106 can be formed from opaque plastic. However, it is desirable to mold the post holder 106 from clear, plastic so that the stud ornament can be seen within the post holder 106 prior to use of the cartridge. Although it is also possible to produce a disposable hand operated cartridge body piercing instrument embodiment of the invention from machined materials, e.g. metals, molded materials are preferred because they can be produced inexpensively, a priority for any disposable product. Embodiments of the invention are preferably provided in a sealed sterilized bubble package such that the device is used one time to provide a piercing with the pre-installed post and then discarded.

FIGS. 1G to 1I illustrate a cross section views of an exemplary hand operated body piercing cartridge embodiment of the invention at different stages of operation. A user positions a body part 120 (of another) against the backing platform 116. The jaw 112 and the main body 102 are moved together by the user's hand, causing the post 108 to pierce the body part 120. Following this, the user allows the jaw 112 and the main body 102 to separate, causing the post 108 to be released from the post holder 106 and remain pierced through the body part 120.

FIG. 1G illustrates a cross section view of the disposable hand operated body piercing cartridge 100 prepared for use. As shown, the post 108 is supported within, the post holder 106 which is within the post holder track 110 of the main housing 102. A body part 120, e.g. an ear lobe, a nostril, navel flap, etc., is positioned against the backing platform 116 of the jaw 112. The jaw 112 is slidably engaged in the jaw track 114 of the main housing. A spring 130 is disposed within the main housing 102 forcing the main housing 102 and, jaw 112 apart to oppose to moving the jaw 112 and main housing 102 together. A catch 126 attached to the jaw 112 and latched against an edge within the main housing 102 prevents the jaw 112 from being forced out of the jaw track 114 of the main housing 102 by the spring 130 force.

FIG. 1H illustrates a cross section view of an exemplary hand operated body piercing cartridge 100 embodiment of the invention compressed to pierce a body part 120. To achieve this, one or more fingers, e.g. the index finger, of a user's hand are positioned across the finger grip section 118 disposed below and opposite the backing platform 116 of the jaw 112 while the thumb of the user's hand is positioned across a thumb grip section 104 along a rear surface of the main body 102. Pressure is applied between the thumb and one or more fingers to move the jaw 112 and the main body 102 together along, the jaw track 114 such that a post 108 pierces the body part 120 against the backing platform 116 of the jaw 112. The sharpened end of the post 108 enters the hole 112 in the backing platform 116 of the jaw 112 after piercing the body pail 120. The spring 130 is compressed against the pressure of the user's hand forcing the jaw 112 and main body 102 together. In addition, a push catch 124, having cantilever spring configuration with a rising slope, is attached to the jaw 112 and has moved back past the post holder 106 and popped up behind it.

Importantly, the jaw 112 includes a stiffener 128 behind the finger grip section 118 aligned parallel with the jaw track 114 which also enters the main housing 102. The stiffener 128 stabilizes movement of the jaw and main body during piercing. Typically, the stiffener comprises a longitudinal stiffener extending from the finger grip section 118 parallel to the jaw track 114 into the main housing 102, although other configurations are possible as will be appreciated by those skilled in the art. The width of the stiffener 128 matches the receiving pocket in the main body 102 to function as an additional jaw track. Accordingly, the pair of offset jaw tracks ensure steady aligned movement of the post 108 to prevent twisting of the jaw 112 and backing platform 116.

FIG. 1I illustrates a cross section view of an exemplary hand operated body piercing cartridge 100 embodiment of the invention released to eject the post holder 106. As the user's hand is released, pressure from the spring 130 forces the jaw 112 and main body 102 apart. As the jaw 112 moves along the jaw track 114 under force from the spring 130, the push catch 124, having previously popped up behind the post holder 106, now pushes the post holder 106 forward and out of the post holder track 110. The post holder 106 comprise two parts which are held together to enclose and support the post 108 only while it is within the post holder track 110 as described in detail hereafter. Once the post holder 106 exits the track 110, the two parts of the post holder 106 separate and release the post 108 pierced through the body part 120.

2.0 Finger and Thumb Grips

Another important feature of the novel cartridge is the inclusion of grips on opposing ends. The grips allow a user to the finger grip section and the thumb grip section each comprise a series of bumps or ridges for improving grip. It should be noted that device can be used and operated with the user's hand inverted, with the thumb and fingers across the finger and thumb grip sections 118, 104, respectively. As such, the different grip sections 118, 104 are identified as they are preferably employed but not required to be employed. Including the grips directly on the cartridge 100 allows a user to perform a piercing without requiring loading the cartridge into a separate instrument or "gun." The cartridge 100 is dispensed from a sterilized packaged, used once to form a piercing of a body part 120, and then discarded. This disposable form cartridge 100 reduces the risk of infection.

3.0 Post Holder and Post with Conical Barb

Embodiments of the invention employ a post 108 supported by a post holder 106 slidably engaged with a post holder track 110 within the main housing 102. Preferably, the post holder 106 comprises separate portions which are held together as long as the post holder 106 is slidably engaged within the post holder track 110, but fall away to release the post 108 after exiting the post holder track 110. For example, the separate portions can comprise two halves 202A, 202B each having half a socket 206A, 206B for the stud ornament of the post 108 which mate together fully enclosing the stud ornament of the post 108 and allowing the sharpened post end to extend from the post holder 106. In addition, the two halves can be further aligned together by a pin 204A on one half and a matching socket 204B on the other that engage one, another when assembled around the post 108.

FIGS. 2A and 2B illustrate isometric views of an exemplary post holder 106 for use in a hand operated body piercing cartridge 100 embodiment of the invention. The separate halves 202A, 202B divide along a vertical plane such that each half 202A, 202B comprises a half socket 206A, 206B for the supporting the post 108 when they are coupled together within the post holder track 110 of the main housing 102. To assist in alignment of the two halves 202A, 202B when they are coupled together a matching pin 204A and hole 204B are disposed on each of two halves 202A, 202B on the vertical plane where they separate. The pin 204A and hole 204B can be disposed on either the left and, right, or right and left sides of the post holder 106.

FIGS. 3A to 3C illustrate various views of an exemplary conical barb post for use with a hand operated body piercing cartridge embodiment of the invention. Cartridge embodiments of the invention can employ any suitable post 108 design. The post 108 includes an ornament 302 at one end which is enclosed in the socket formed by the half sockets 206A, 206B of the post holder 106. The half sockets 206A, 206B also form a channel which supports the shaft 304 of the post 108 which extends out of the post holder 106 towards the backing platform 116 of the jaw 112.

The point 306 at the opposite end of the shaft 304 can be any suitable form of sharpened end. For example, the point 306 can comprise a cannula form, a conical point, a barb or any other known point for body piercing. In one notable example, the point 306 comprises a conical barb comprising a pointed conical end which flares to a diameter wider than the shaft 304 diameter. An inverted conical section (having the same taper angle as the pointed conical end) reverses the diameter from the widest diameter to the shaft 304 diameter. This conical barb shape allows a body piercing to be formed, e.g. through a nostril, and remain in place without requiring a clutch to secure the pointed end. The widened conical barb prevents the post from falling out in a clutchless piercing.

4.0 Main Housing Tracks

Figure 4A:
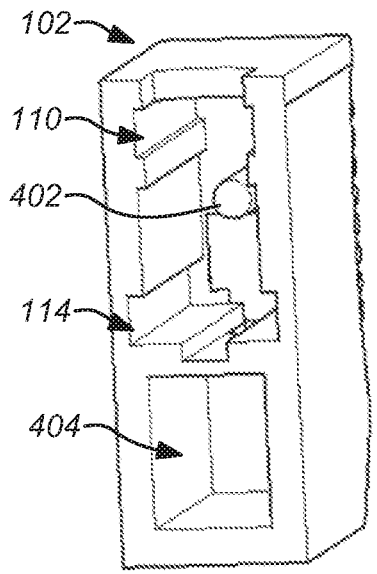
FIG. 4A illustrates a front isometric view of an exemplary main housing, for use in a hand operated body piercing cartridge embodiment of the invention.
Figure 4B:
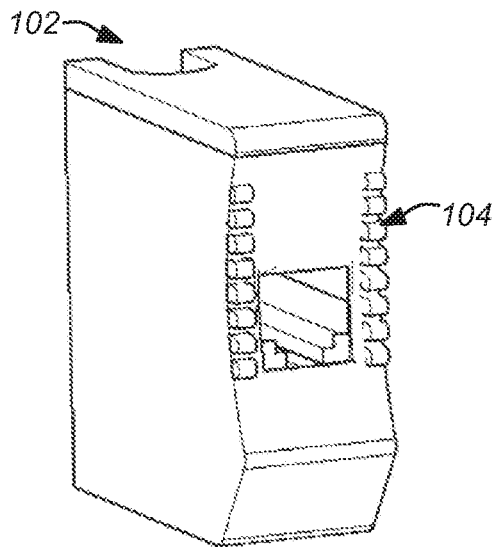
FIG. 4B illustrates a back isometric view of an exemplary main housing for use in a hand operated body piercing cartridge embodiment of the invention.
Figure 4C:
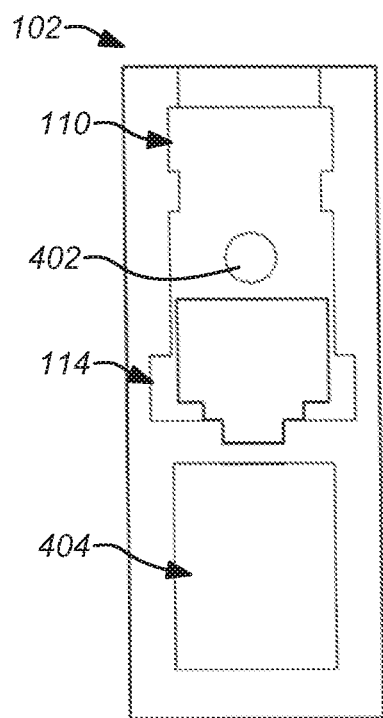
FIG. 4C illustrates a front view of an exemplary main housing for use in a hand operated body piercing cartridge embodiment of the invention.

FIGS. 4A to 4C illustrate various views of an exemplary main housing 102 for use in a hand operated body piercing cartridge embodiment of the invention. The main housing 102 includes the post holder track 110 and the jaw track 114. In addition, the main housing 102 includes the recess 404 for receiving the stiffener 128 affixed to the jaw 112 which functions as an additional track as previously described. It should be noted that different shapes of the post holder track 110, the jaw track 114 and the recess 404 can be varied. It is only necessary that they present projected cross sections matching the respective element portions, i.e. the post holder 106, the jaw 112, and the stiffener 128, that they receive to provide slidable engagement therewith.

As previously mentioned, the jaw 112 includes a catch 126 for holding the jaw 112 engaged in the jaw track 114 of the main housing 102 against the spring 130 forcing the jaw 112 and the main housing 102 apart. The catch 126 is designed to engage a horizontal edge at the bottom of the jaw track 114 disposed at the position of the catch 126 shown in FIG. 1I. In addition, the main housing 102 also includes a spring engagement pin 402 for securing the cylindrical compression spring 130 in position when the cartridge 100 is assembled. This matches the spring engagement socket 502 of the jaw 112 described hereafter.

5.0 Jaw and Backing Platform

Figure 5B:
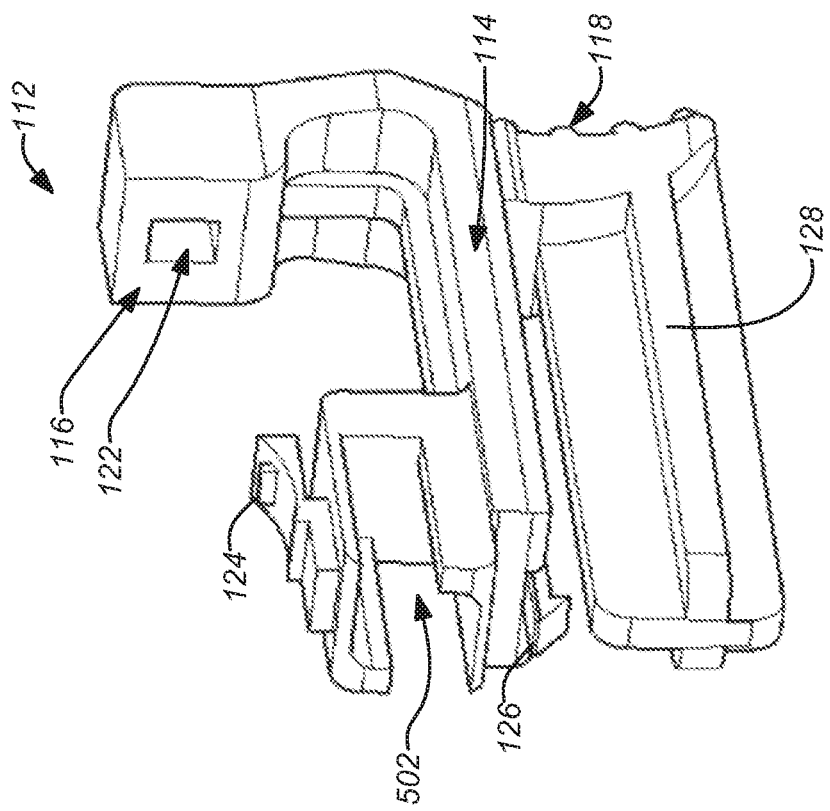
FIG. 5B illustrates a right back isometric view of an exemplary jaw for use in a hand operated body piercing cartridge embodiment of the invention.
Figure 5A:
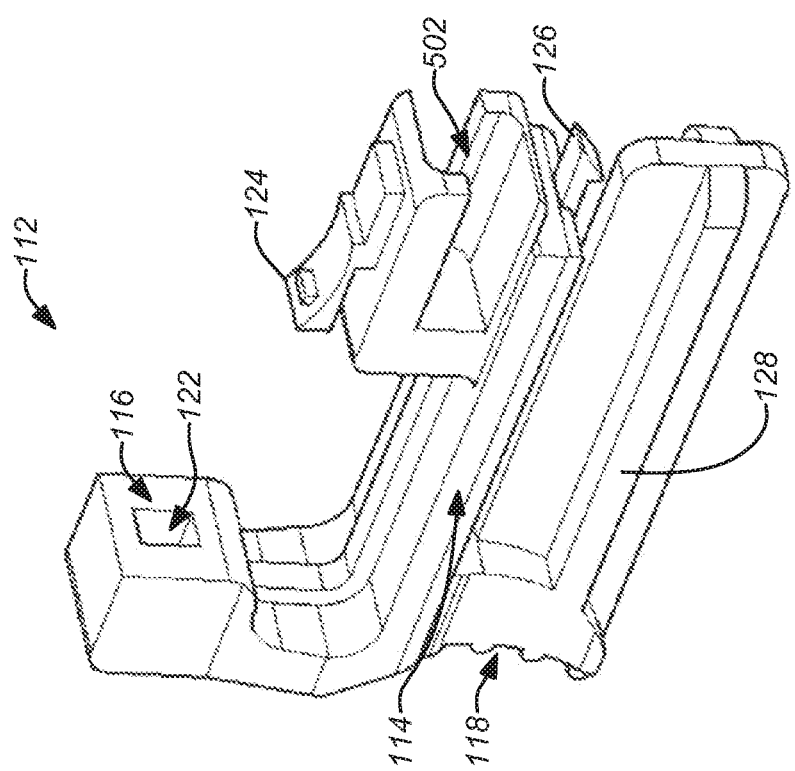
FIG. 5A illustrates a left back isometric view of an exemplary jaw for use in a hand operated body piercing cartridge embodiment of the invention.
Figure 5C:
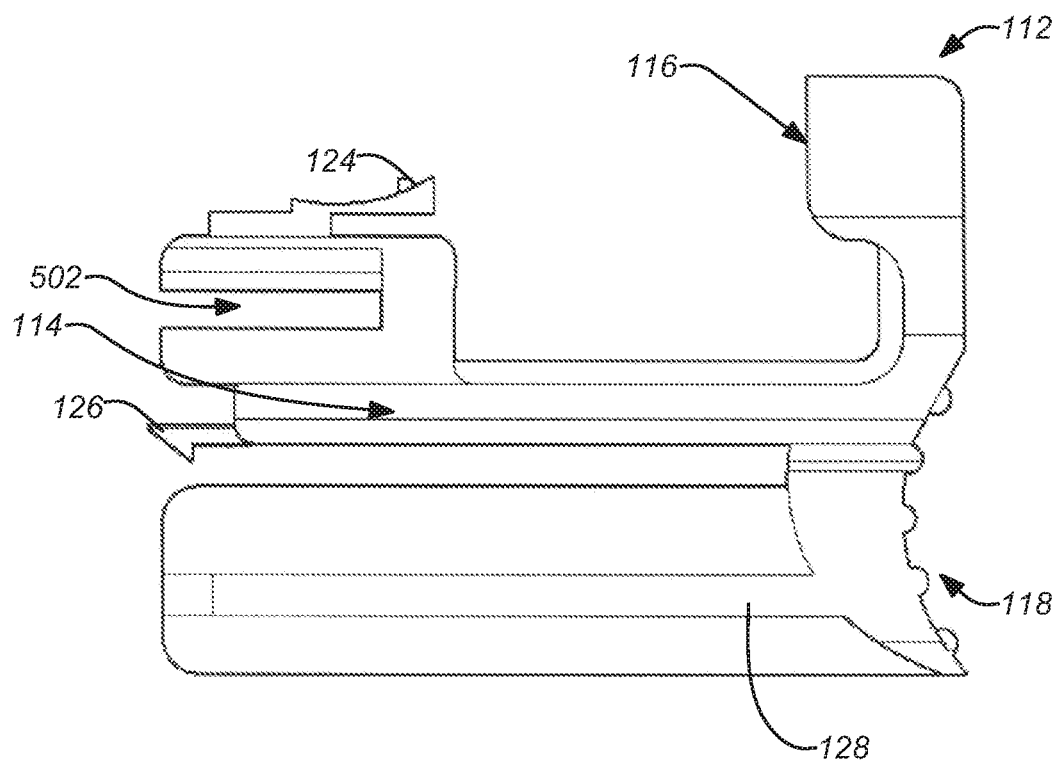
FIG. 5C illustrates a side view of an exemplary jaw for use in a hand operated body piercing cartridge embodiment of the invention.

FIGS. 5A to 5C illustrate various views of an exemplary jaw for use in a hand operated body piercing cartridge embodiment of the invention. The backing platform 116 can comprise a surface for supporting a user body part in an area around a back side of a piercing location and hole 122 therethough aligned with the post 108. The hole 122 therethough can be vertically elongated to accommodate some vertical movement by the post 108 during piercing. In some instances, the jaw 112 can include a reinforcing beam or stiffener 128 disposed behind and aligned with the finger grip section 118 to stabilize movement of the jaw 112 and main body 102 during piercing.

Figure 6:
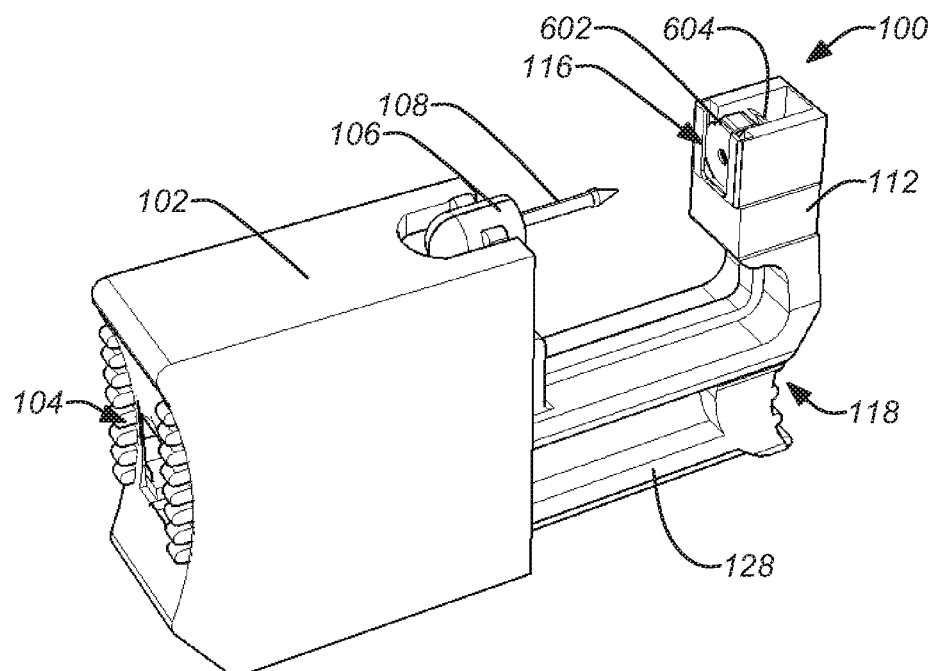
FIG. 6 illustrates a hand operated body piercing cartridge embodiment of the invention including a jaw with an optional clutch.

FIG. 6 illustrates a hand operated body piercing cartridge embodiment of the invention including a jaw 112 with an optional clutch 602. As shown, the backing platform 116 can optionally house a clutch 602 disposed in a vertical slot to engage the post 108 during piercing and then slide out of the vertical slot. A spring finger 604 is disposed behind the clutch 602 applying a small amount of pressure to the clutch 602 in order to prevent it from slipping out until after the clutch 602 is engaged with the post 108. In this example, the clutch 602 surface functions in part as the backing platform 116. Any suitable known clutch 602 can be adapted to function with the jaw 112 of the device 100.

Significantly, the jaw 112 can include a push catch 124 for sliding past the post holder 106 as the jaw 112 and main housing 102 are moved together during piercing to engage a back end of the post holder 106. The push catch 124 then pushes the post holder 106 out of the post holder track 110 as the spring 130 forces the jaw 112 and main housing 102 apart after piercing.

6.0 Hand Operated Body Piercing Cartridge Method

Figure 7:
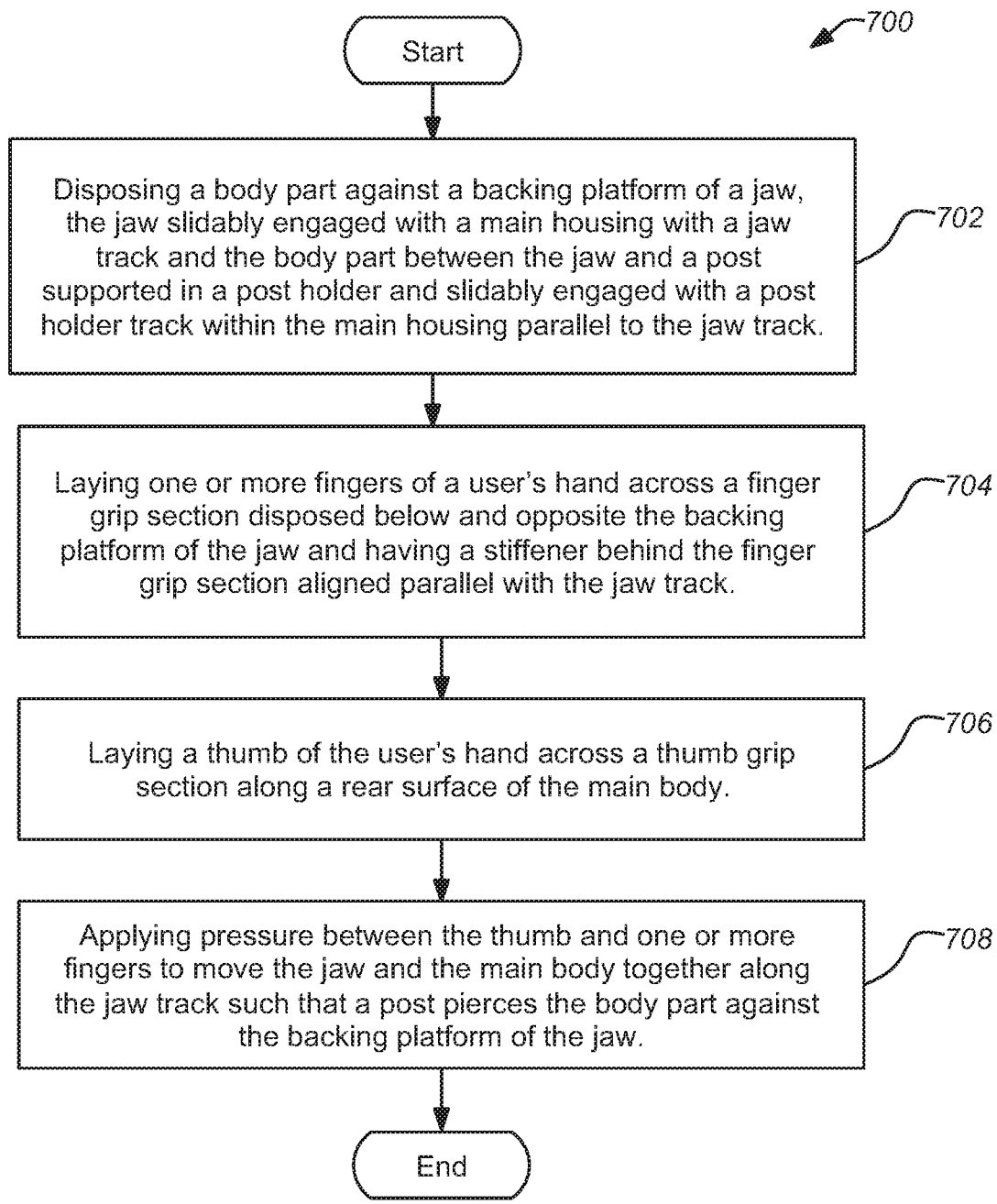
FIG. 7 is a flowchart of an exemplary method of operating a hand operated body piercing cartridge embodiment of the invention.

FIG. 7 is a flowchart of an exemplary method, of operating a hand operated body piercing cartridge embodiment of the invention. The method 700 begins with the step 702 of disposing a body part against a backing platform of a jaw, the jaw slidably engaged with a main housing with a jaw track and the body part between the jaw and a post supported in a post holder and slidably engaged with a post holder track within the main housing parallel to the jaw track. One or more fingers of a user's hand are laid across a finger grip section disposed below and opposite the backing platform of the jaw and having a stiffener behind the finger grip section aligned parallel with the jaw track in step 704. A thumb of the user's hand is laid across a thumb grip section along a rear surface of the main body in step 706. Pressure is applied between the thumb and one or more fingers to move the jaw and the main body together along the jaw track such that a post pierces the body part against the backing platform of the jaw in step 708.

This concludes the description including the preferred embodiments of the present invention. The foregoing description of the preferred embodiment of the invention has been presented for the purposes of illustration and description. It is not intended to be exhaustive or to limit the invention to the precise form disclosed. Many modifications and variations are possible in light of the above teaching.

It is intended that the scope of the invention be limited not by this detailed description, but rather by the claims appended hereto. The above specification, examples and data provide a complete description of the manufacture and use of the apparatus and method of the invention. Since many embodiments of the invention can be made without departing from the scope of the invention, the invention resides in the claims hereinafter appended.

What is claimed is:

1. A body piercing instrument cartridge, comprising:
a main housing having a thumb grip section along a rear surface;
a post holder supporting a post and slidably engaged with a post holder track within the main housing; and
a jaw slidably engaged with the main housing with a jaw track, the jaw track parallel to the post holder track, and the jaw supporting a backing platform for piercing a body part with the post as the jaw and main housing are moved together along the jaw track, the jaw including a finger grip section disposed below and opposite the backing platform and opposite the thumb grip section of the main housing;
wherein the jaw includes a stiffener disposed behind finger grip section and the stiffener disposed in an additional track between the main housing and the jaw.

2. The body piercing instrument cartridge of claim 1, wherein the stiffener comprises a longitudinal stiffener extending from the finger grip section parallel to the jaw track into the main housing.

3. The body piercing instrument cartridge of claim 1, wherein the stiffener stabilizes movement of the jaw and main body during piercing.

4. The body piercing instrument cartridge of claim 1, wherein the post holder includes separate portions held together to support the post while slidably engaged with the post holder track within the main housing such that the separate portions fall away to release the post after exiting the post holder track.

5. The body piercing instrument cartridge of claim 1, further comprising a spring disposed between the main housing and the jaw to oppose to moving the jaw and main housing together.

6. The body piercing instrument cartridge of claim 5, wherein the jaw includes a catch for holding the jaw engaged in the jaw track of the main housing against the spring forcing the jaw and the main housing apart.

7. The body piercing instrument cartridge of claim 5, wherein the jaw includes a push catch for sliding past the post holder as the jaw and main housing are moved together during piercing to engage a back end of the post holder and push the post holder out of the post holder track as the spring forces the jaw and main housing apart after piercing.

8. The body piercing instrument cartridge of claim 1, wherein the backing platform comprises a surface for supporting a user body part in an area around a back side of a piercing location and a hole therethough aligned with the post.

9. The body piercing instrument cartridge of claim 8, wherein the hole therethough is vertically elongated to accommodate some vertical movement by the post during piercing.

10. The body piercing instrument cartridge of claim 1, wherein the post comprises a conical barb for clutchless piercing.

11. The body piercing instrument cartridge of claim 1, wherein the backing platform houses a clutch disposed in a vertical slot to engage the post during piercing and then slide out of the vertical slot.

12. The body piercing instrument cartridge of claim 1, wherein the finger grip section and the thumb grip section each comprise a series of bumps or ridges for improving grip.

* * * * *